(12) United States Patent
Perreau et al.

(10) Patent No.: US 9,139,879 B2
(45) Date of Patent: Sep. 22, 2015

(54) TAM RECEPTORS AND TAM RECEPTOR LIGANDS IN DETECTION AND MODULATION OF NEUROPATHOLOGICAL DISEASE

(75) Inventors: Victoria Mary Perreau, Parkville (AU); Judith Field, Parkville (AU); Michele D Binder, Parkville (AU); Trevor Kilpatrick, Parkville (AU)

(73) Assignee: HOWARD FLOREY INSTITUTE, Parkville, Victoria (AU)

( * ) Notice: Subject to any disclaimer, the term of this patent is extended or adjusted under 35 U.S.C. 154(b) by 0 days.

(21) Appl. No.: 13/817,131

(22) PCT Filed: Aug. 19, 2011

(86) PCT No.: PCT/AU2011/001070
§ 371 (c)(1),
(2), (4) Date: Jul. 12, 2013

(87) PCT Pub. No.: WO2012/021942
PCT Pub. Date: Feb. 23, 2012

(65) Prior Publication Data
US 2013/0309243 A1    Nov. 21, 2013

(30) Foreign Application Priority Data
Aug. 19, 2010 (AU) .............................. 2010903728

(51) Int. Cl.
| | | |
|---|---|---|
| *A61K 39/39* | (2006.01) | |
| *C12Q 1/68* | (2006.01) | |
| *G01N 33/68* | (2006.01) | |
| *A61K 39/395* | (2006.01) | |
| *C07K 16/28* | (2006.01) | |

(52) U.S. Cl.
CPC .......... *C12Q 1/6883* (2013.01); *A61K 39/3955* (2013.01); *C07K 16/2863* (2013.01); *G01N 33/6896* (2013.01); *C12Q 2600/158* (2013.01); *G01N 2333/91215* (2013.01); *G01N 2800/285* (2013.01); *G01N 2800/56* (2013.01)

(58) Field of Classification Search
CPC ........................... A61K 39/395; C07K 16/2863
See application file for complete search history.

(56) References Cited

U.S. PATENT DOCUMENTS

| | | | |
|---|---|---|---|
| 5,538,861 A | 7/1996 | Schneider et al. | |
| 2005/0186571 A1 | 8/2005 | Ullrich et al. | |
| 2006/0003327 A1 | 1/2006 | Achiron et al. | |

FOREIGN PATENT DOCUMENTS

| | | |
|---|---|---|
| WO | WO 03/039575 A2 | 5/2003 |
| WO | WO 2010/008411 A1 | 1/2010 |

OTHER PUBLICATIONS

't Hart et al.,Modelling of multiple sclerosis: lessons learned in a non-human primate, Oct. 2004, Lancet Neurol. 3: 588-597.*
Wekerle et al., Animal models of multiple sclerosis, 2006, Drug Discovery Today: Disease Models 3(4):359-367.*
Binder, M.D., et al., 2008, "Gas6 Deficiency Increases Oligodendrocyte Loss and Microglial Activation in Response to Cuprizone-Induced Demyelination," *The Journal of Neuroscience*, 28: 5195-5206.
Binder, M.D., et al., 2009, "TAM Receptor Signalling and Demyelination," *Neurosignals*, 17: 277-287.
Sainaghi P.P., et al., 2008, "Elevation of Gas6 protein Concentration in Cerebrospinal Fluid of Patients with Chronic Inflammatory Demyelinating Polyneuropathy (CIDP)," *Journal of Neurological Sciences*, 269: 138-142.
Weinger, J.G., et al., 2009, "Up-Regulation of Soluble Axl and Mer Receptor Tyrosine Kinases Negatively Correlates with Gas6 in Established Multiple Sclerosis Lesions," *The American Journal of Pathology*, 175: 283-293.
Binder, M.D. et al. 2010 "Gas6 deficiency increases damage but does not inhibit initial recovery in response to cuprizone-induced demyelination" Society for Neuroscience Meeting, Program/Poster No. 257.1/T9 (in 2 pages).
Binder, M.D. et al. 2011 "Gas6 Increases Myelination by Oligodendrocytes and Its Deficiency Delays Recovery following Cuprizone-Induced Demyelination" *PLOS One* 6: e17727 (in 11 pages).
Sellebjerg, F. et al. 2009 "Increased cerebrospinal fluid concentrations of the chemokine CXCL13 in active MS" *Neurology* 73: 2003-2010.
Supplementary European Search Report in corresponding European Application No. 11 81 7585, dated Mar. 13, 2014.
Kipp, M. et al. 2009 "The cuprizone animal model: new insights into an old story" *Acta Neuropathol* 118: 723-736.

* cited by examiner

*Primary Examiner* — John Ulm
(74) *Attorney, Agent, or Firm* — Knobbe, Martens, Olson & Bear, LLP

(57) ABSTRACT

Methods, compositions and kits based on TAM receptors, or TAM receptor ligands or agonists are for detection of neuropathological diseases or determination of their progression. The neural diseases include multiple sclerosis or other inflammatory neural disorders that are characterized by demyelination, oligodendrocyte cytotoxicity and microglial activation. These methods include screening cells of a subject where identification of an elevation of expression of a TAM receptor or a change in expression of a TAM receptor ligand indicates the presence of the disease presence or progression. In addition, subjects with such neuropathological diseases can be treated by administering TAM receptor ligands (such as GAS 6 or Protein S) or by administering agonists such as antibodies specific for the TAM receptors; Axl, Mer or Tyro3.

2 Claims, 9 Drawing Sheets

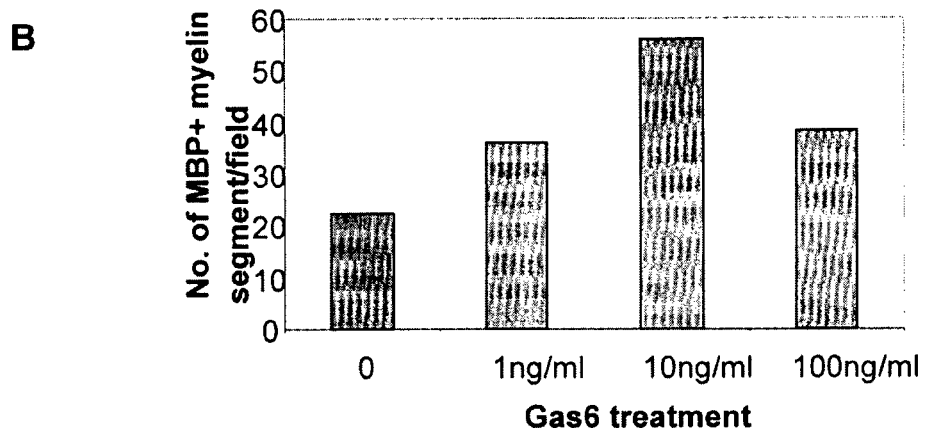
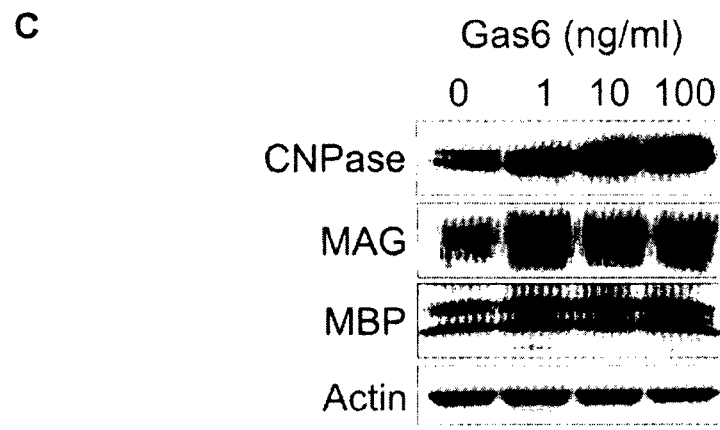
Figure 5B and C

One way ANOVAs:
CD68 = 0.0003
Mac1 = 0.0016

TAM RECEPTORS AND TAM RECEPTOR LIGANDS IN DETECTION AND MODULATION OF NEUROPATHOLOGICAL DISEASE

FILING DATA

This application is associated with and claims priority from Australian Provisional Patent Application No. 2010903728, filed on 19 Aug. 2010, entitled "A method of diagnosis and treatment", the entire contents of which, are incorporated herein by reference.

FIELD

The present disclosure relates generally to the field of inflammatory neuropathology. The present disclosure enables the diagnosis and monitoring of inflammatory neuropathologies such as demyelinating disease, oligodendrocyte cytotoxicity and microglial activation and other neurodegenerative conditions and screening for medicaments in the treatment and prophylaxis of such conditions. Diagnostic kits, high through-put screening, and therapeutic compositions for inflammatory neuropathies are also taught herein.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Receptor protein tyrosine kinases (PTKs) are cell surface transmembrane receptors which, upon binding of an extracellular ligand, triggers receptor dimerization and kinase activity. Signal transduction cascades initiated by PTK activation control a range of cellular processes including cell differentiation and apoptosis. One particular group of PTK receptors is the TAM family of receptors (Lai and Lemke, *Neuron* 6:691-704, 1991). Three members of this family have been identified to date designated Axl, Mer and Tyro3 (reviewed by Lemke and Rothlin, *Nature Reviews (Immunology)* 8:327-336, 2008). TAM receptor-mediated signaling is associated with tissue homeostasis in the nervous, reproductive and vascular systems. TAM signaling is also important in regulating innate immune systems including inhibiting the inflammatory response to pathogens and apoptotic cells by dendritic cells and macrophages and maturation of natural killer cells.

TAM receptors and their ligands crystallise as homo- and hetero-dimers. Each monomeric form of the receptor comprises an N-terminal region, a Gla-domain, a EGF-like domain, an immunoglobulin-like domain, a transmembrane domain and a PTK domain (Lemke and Rothlin, 2008 supra).

Demyelinating disease is a nervous system disorder in which the myelin sheath of neurons is damaged. This reduces signal transmission in affected nerves causing inter alia impairment of sensation, movement and cognition. Demyelinating disease encompasses multiple sclerosis (MS) and other idiopathic inflammatory demyelinating diseases. A proportion of patients which present with a first demyelinating event (FDE), also known as a clinically isolated syndrome (CIS) go onto develop MS. The early course of MS including the number of relapses in the first two years, is predictive of early development of permanent disease. One form of predictor of disease activity and the likelihood of progression from an FDE to MS is with an MRI (Brex et al., *N. Engl. J. Med* 346(3):158-164, 2002). The MRI detects lesions. Patients with no lesions have an 11% chance of MS and patients with two or more lesions have an 83-88% of MS, all within a 10 year period (Barkinof et al., *Brain* 120:2059-2069, 1997; O'Riorden et al., *Brain* 121:495-503, 1998). Whilst MRI is a useful tool, it is expensive and requires specialist equipment and training.

Oligodendrocytes are a major cell type damaged in these MS and other idiopathic inflammatory demyelinating diseases. Hence, the term "oligodendrocyte disease" is used to define demyelinating diseases which affect the oligodendrocytes and their ability to interact with various cell types in the demyelinating area. The TAM family of receptors has been found to be expressed in the nervous system including oligodendrocytes (Binder et al., *The Journal of Neuroscience* 28(2):5195-5206, 2008). Oligodendrocyte death is an early event in demyelinating disease (Barnett and Prineas, *Ann. Neurol* 55:459-468, 2004).

In accordance with the present disclosure, it has been determined that TAM receptors are a useful bio-indicator of demyelination and of oligodendrocyte survival and microglial modulation. The development of a molecular determinant of MS and other idiopathic inflammatory demyelinating disease enables early diagnosis and intervention and improve clinical outcomes for patients.

SUMMARY

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

The present disclosure teaches bio-indicators of inflammatory neuropathological conditions which encompass a spectrum of neurodegenerative diseases and conditions. The bio-indicators are the TAM receptors and their ligands. It is determined herein that up-regulated levels of a TAM receptor and/or a change in levels of a TAM receptor ligand correspond to the presence of an inflammatory neuropathological condition or a pre-disposition for the development of same.

The bio-indicators taught by the present disclosure are instructional for prediction, diagnosis, prognosis and monitoring of disease progression and are useful therapeutic targets for medicaments for the treatment or prophylaxis of inflammatory neuropathologies. The bio-indicators are also considered biomarkers and diagnostic targets. The biomarkers may be used alone or in combination with other diagnostic protocols including MRI.

Accordingly, an aspect enabled herein is a method for detecting the presence of an inflammatory neuropathological condition or disease in a subject, the method comprising screening cells from the subject for expression of a TAM receptor or a ligand thereto wherein elevated expression of the receptor or a change in expression of the ligand is indicative of the presence of the inflammatory neuropathological disease or condition or a likelihood of developing same. By "expression" is meant assaying for level of protein (i.e. TAM receptor or TAM receptor ligand) or assaying for changes in expression of genes encoding the TAM receptor (or a monomeric form thereof) or its ligand. An elevation in TAM receptor protein or mRNA encoding same or a change relative to a normal control or a control from a subject with known disease states of its ligand (at the protein or mRNA level) is indicative of the inflammatory neuropathology.

Another aspect taught herein provides a method for detecting the presence of an inflammatory neuropathological condition or disease in a subject, the method comprising screening cells from the subject for expression of a TAM receptor or ligand or gene encoding the receptor or ligand wherein an elevated expression of the receptor or a change in expression of its ligand is indicative of the presence of the inflammatory neuropathological disease or condition or a likelihood of development of same. For sake of brevity, the term "expression" is used for gene expression and protein levels.

In an embodiment, the inflammatory neuropathological disease or condition is a demyelination event such as an inflammatory idiopathic neuropathological disease or condition. Such a disease or condition includes multiple sclerosis (MS) or a related condition such as acute disseminated encephalomyelitis, optic neuropathy (including neuromyelitis optic with transient autonomic disturbances), Devic's neuromyelitis optica, tropical spastic paraparesis, non-compressive myelopathies, concentric sclerosis, diffuse sclerosis acute hemorrhagic leukoencephalogpathy, metabolic leukodystrophy, leukoaraiosis, acute disseminated encephalomyelitis, progressive multi focal leukoencephalogpathy, multisystem atrophy and in the repair of demyelination-associated disease or trauma. All such inflammatory neuropathologies are also encompassed by the term "neurodegenerative disease or condition". A subject may also present asymptomatically but nevertheless be treated to prevent or delay development of the condition.

An inflammatory neuropathology includes and inflammatory neurodegenerative disease or condition and in particular neurodegenerative conditions involving oligodendrocyte cytotoxicity or cell cycle arrest, demyelination and/or microglial activation.

Also taught by the present disclosure is an assay for monitoring an inflammatory neuropathology. Such monitoring is useful following therapeutic intervention or as part of the decision process for initiating therapy. By "therapy" includes administration of a medicament as well as behavioral intervention. This aspect includes monitoring patients presenting with a first demyelinating event (FDE) and those at risk of developing an FDE.

Hence, the present disclosure is further directed to a method for monitoring progression of an inflammatory neuropathological condition in a subject, the method comprising screening cells from the subject for expression of a TAM receptor or a ligand thereto over time wherein a change in expression of the receptor or its ligand within a time period is indicative of disease progression. Detection may be at the protein level or gene expression level.

By "disease progression" is meant a monitoring of an amelioration of symptoms or a worsening of symptoms of the inflammatory neuropathology. In an embodiment, a decrease in the level of expression of a TAM receptor or a change in ligand levels such as during therapy provides an indication of an improving disease outcome or state.

Notwithstanding that TAM receptor expression is up-regulated in a disease situation, promoting TAM receptor-mediated signaling is proposed herein to ameliorate symptoms of an inflammatory neuropathological condition or disease. Hence, another aspect taught herein is a method for detecting the presence of an inflammatory neuropathological condition or disease in a subject, the method comprising screening cells of the subject for extent of signaling mediated via a TAM receptor or a ligand thereto wherein a decrease in TAM receptor-mediated signaling is indicative of the presence of an inflammatory neuropathological disease or condition or a likelihood of developing same.

Reference to a "TAM receptor" includes Axl, Mer and Tyro3 or a functional equivalent thereof. The TAM receptor may be in homomultimeric or heteromultimeric form or it may be in monomeric pre-receptor form. In an embodiment, the "multimer" is a dimer, hence, a homodimer or heterodimer. Reference to a "TAM receptor ligand" includes Gas6 (Growth Arrest Gene 6) and Protein S or a functional equivalent thereof. A TAM receptor ligand also includes an antibody to the TAM receptor complex or to monomeric forms or heteromultimeric or homomultimeric forms of the receptor.

Another aspect taught herein is an agonist of a TAM receptor ligand such as an agonist of Gas6 or Protein S and an agonist of a TAM receptor itself, which agonists facilitate TAM receptor-mediated signaling.

The present disclosure teaches a method for the treatment or prophylaxis of an inflammatory neuropathological disease or condition in a subject, the method comprising administering to the subject an effective amount of a TAM receptor agonist or a TAM receptor ligand modulator for a time and under conditions sufficient to ameliorate symptoms of the inflammatory neuropathological disease or condition. The ligand modulator may be an agonist or antagonist.

A "TAM receptor agonist" and a "TAM receptor ligand agonist" includes a "TAM receptor-mediated signaling agonist". An example of such an agonist is a mimetic of Gas6 or Protein S. Another example of an agonist is an antibody to a monomeric form of the TAM receptor which facilitates dimerization or multimerization and promotes signaling.

The agonist may, therefore be an agonist of a TAM receptor ligand or of a TAM receptor or may otherwise facilitate TAM receptor-mediated signaling. As indicated above, the inflammatory neuropathological disease or condition includes a demyelinating disease.

A high throughput screen for agonists of TAM receptor-mediated signaling is also contemplated herein. Antagonists of the receptor ligand are also contemplated herein.

The present disclosure further enables use of TAM receptor-mediated signaling in the manufacture of an assay to detect an inflammatory neuropathology. The present disclosure also teaches the use of an agonist of TAM receptor-mediated signaling in the manufacture of a medicament in the treatment of an inflammatory neuropathological disease or condition.

Abbreviations used herein are summarized in Table 1.

TABLE 1

| Abbreviations | |
|---|---|
| Abbreviation | Definition |
| Axl | A TAM receptor |
| EAE | Experimental autoimmune encephalitis |
| Gas6 | Ligand of a TAM receptor (Growth arrest gene 6) |
| Gas6$^{-/-}$ | Genotype of Gas6 homozygous knockout |
| IBAl | Marker of expression in microglia |
| Mer | A TAM receptor |
| MS | Multiple sclerosis |
| Protein S | Ligand of a TAM receptor |
| PTK | Protein tyrosine kinase |
| Tyro3 | A TAM receptor |

BRIEF DESCRIPTION OF THE FIGURES

Some figures contain color representations or entities. Color photographs are available from the Patentee upon

FIGS. 5A through C are photographic and graphical representations showing that exogenous Gas6 increases myelination in vitro.

DETAILED DESCRIPTION

Figure 1:
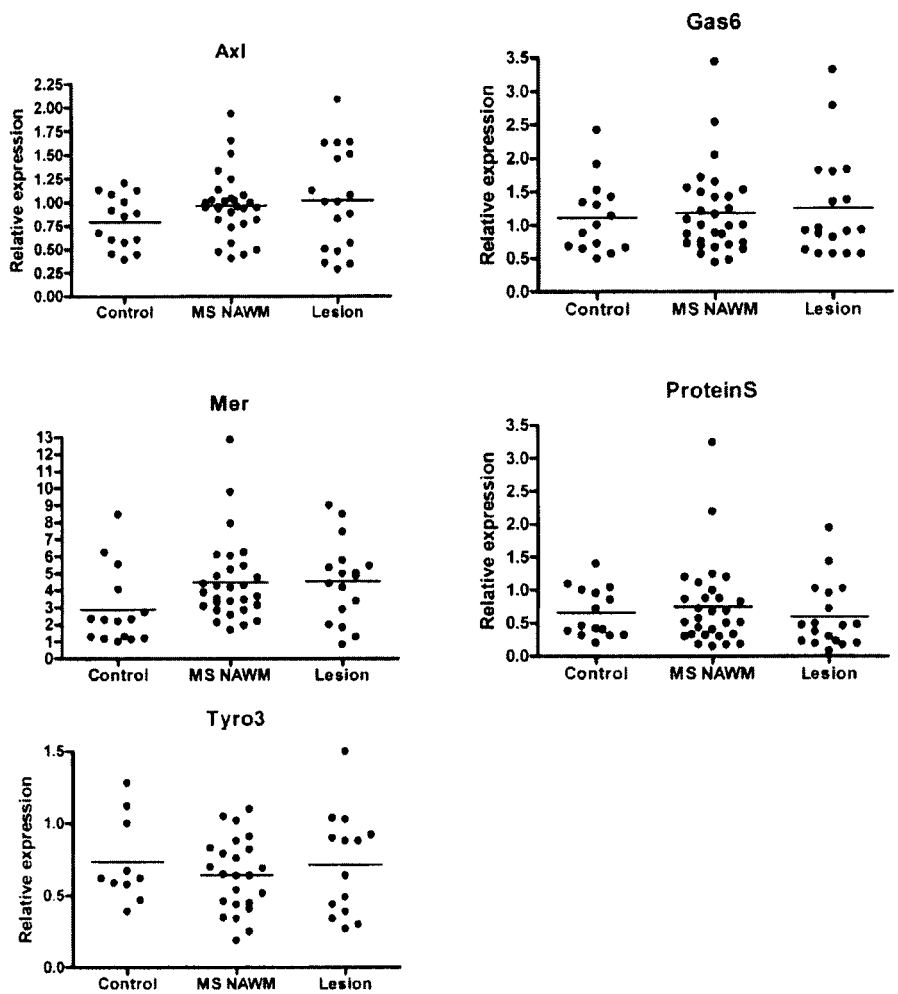
FIG. 1 is a graphical representation of expression of Axl, Gas6, Mer. Protein S and Tyro3 in MS lesions.
Figure 2:
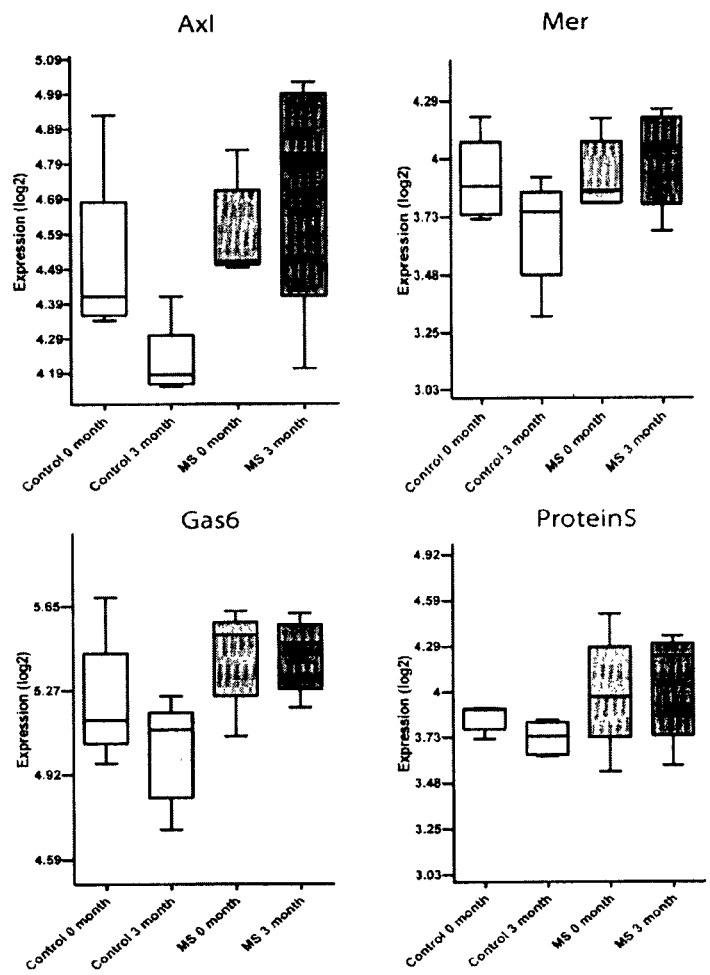
FIG. 2 is a graphical representation of Axl, Mer, Gas6 and Protein S gene expression in blood cells.

As used in the subject specification, the singular forms "a", "an" and "the" include plural aspects unless the context clearly dictates otherwise. Thus, for example, reference to "a TAM receptor" includes a single TAM receptor, as well as two or more TAM receptors; reference to "an agonist" or "an inflammatory neuropathology" includes a single agonist or single inflammatory neuropathology, as well as two or more agonists or inflammatory neuropathologies; reference to "the disclosure" includes a single or multiple aspects taught by the disclosure; and so forth. All aspects and embodiments described herein are encompassed by the term "invention".

The present disclosure teaches that TAM receptors are up-regulated and the levels of TAM receptor ligands are altered during or prior to development of an inflammatory neuropathological disease or condition such as during or prior to oligodendrocyte disease including inflammatory demyelinating disease. "Up-regulation" means that there is enhanced or elevated levels relative to normal (non-disease condition) cells of TAM receptor or ligand mRNA or protein. It does not mean enhanced TAM receptor-mediated signaling. By "altered" means an up- or down-regulation compared to a normal control. Disease conditions contemplated herein include MS, acute disseminated encephalomyelitis, optic neuropathy (including neuromyelitis optic with transient autonomic disturbances) Devic's neuromyelitis optica, tropical spastic paraparesis, non-compressive myelopathies, concentric sclerosis, diffuse sclerosis acute hemorrhagic leukoencephalopathy, metabolic leukodystrophy, leukoaraiosis, acute disseminated encephalomyelitis, progressive multifocal leukoencephalopathy, multisystem atrophy and repairing the demyelination associated with disease or trauma. All these disease conditions are encompassed by the term neurodegenerative disease or condition. These conditions include presymptomatic forms of the condition as well as subjects who present asymptomatically but who are at risk of developing the condition.

The inflammatory neuropathologies contemplated herein include oligodendrocyte diseases such as apoptosis or death of oligodendrocytes or other cytotoxic events involving oligodendrocytes as well as oligodendrocyte cell cycle arrest or demyelination. The inflammatory neuropathology may also involve microglial activation.

Accordingly, an aspect enabled herein is a method for detecting the presence of an inflammatory neuropathological condition or disease in a subject, the method comprising screening cells from the subject for expression of a TAM receptor or ligand thereto wherein elevated expression of the receptor or a change in level of expression of its ligand is indicative of the presence of the inflammatory neuropathological disease or condition or a likelihood of developing same.

Another aspect taught herein provides a method for detecting the presence of an inflammatory neuropathological condition or disease in a subject, the method comprising screening cells from the subject for expression of a TAM receptor or ligand or gene encoding the receptor or ligand wherein an elevated expression of the receptor or a change in expression of its ligand is indicative Of the presence of the inflammatory neuropathological disease or condition or a likelihood of development of same. For sake of brevity, the term "expression" is used for gene expression and protein levels.

In an embodiment, the TAM receptor ligand is elevated. In another embodiment, it is reduced. These levels are relative to a normal control or a sample from a subject with a known disease status. The term "modulated levels" of the ligand is used to describe its altered levels. The levels are compared to a normal control or to a control from a subject with known disease status.

Another aspect taught herein is a method for detecting the presence of a demyelinating disease or condition in a subject, the method comprising screening cells from the subject for expression of a TAM receptor or ligand thereof wherein elevated expression of the TAM receptor or an altered level of expression of its ligand is indicative of the presence of the demyelinating disease or condition or a likelihood of developing same. In an embodiment, the altered level is an elevated level of ligand.

The present disclosure is also instructional for a method for detecting the presence of a neurodegenerative disease or condition in a subject, the method comprising screening cells from the subject for expression of a TAM receptor or ligand thereof wherein elevated expression of the TAM receptor or an altered level of expression of its ligand is indicative of the presence of the neurodegenerative disease or condition or a likelihood of developing same.

An example of a demyelinating disease is an inflammatory idiopathic demyelinating disease such as MS.

In an aspect, a method is enabled for detecting the presence of MS is contemplated in a subject, the method comprising screening cells from the subject for expression of a TAM receptor or a ligand thereto wherein elevated expression of the TAM receptor or an altered level of expression of its ligand is indicative of the presence of MS or a risk of developing same.

Hence, the subject disclosure teaches that:

(i) an increase in TAM receptor protein (including monomeric, homodimeric or heterodimeric forms); and/or (ii) an increase or decrease in one or more TAM receptor ligands; and/or (iii) a change in gene expression levels encoding the receptor or ligand;

is/are associated with an inflammatory neuropathological condition or disease. These levels are compared to a normal control or a control from a subject with known disease status.

The assay described herein may be used alone or in conjunction with other diagnostic protocols such as MRI. Furthermore, the use of a molecular determinant of MS or other inflammatory neuropathology is useful in patients presenting with an FDE or who are being monitored after early onset of symptoms of a disease or who are at risk of developing an FDE. A subject may be asymptomatic but is at risk of developing an FDE or other condition. The present disclosure teaches, therefore, a method for screening a patient with an FDE, the method comprising screening cells from the subject for expression of a TAM receptor or ligand thereof wherein elevated expression of the TAM receptor or a change in level of expression of its ligand is indicative of the presence of the neurodegenerative disease or condition or a likelihood of developing same.

A "TAM receptor" includes monomeric or multimeric (homo- or hetero-merit) forms of Axl, Mer and Tyro3. A TAM receptor ligand includes Gas6 and Protein S. Reference to the receptor or ligand includes its derivatives, homologs and functional equivalents. The term "functional equivalent" also encompasses a mimetic of a TAM receptor ligand which acts as an agonist including biological or chemical molecules capable of this activity.

The method taught herein may be referred to inter alia as an assay, screen, predictor, method, test, system, diagnosis, prognosis, bioassay, determination or report. The method is useful for monitoring disease progression such as following medicament intervention or behavioral modification. Hence, by "therapy" is meant the use of medicaments and behavioral intervention.

Hence, the present disclosure teaches a method for monitoring progression of an inflammatory neuropathological condition in a subject including in a presymptomatic phase of the condition or an asymptomatic subject at risk of developing the condition, the method comprising screening cells from the subject for expression of a TAM receptor or a ligand thereto over time wherein a change in expression of the receptor or its ligand within a time period is indicative of disease progression. This change is relative to a normal control or a control from a subject of known disease status.

Yet another aspect enabled herein is a method for detecting the presence of an inflammatory neuropathological condition or disease or monitoring its progression in a subject, the method comprising screening cells of the subject for expression of a TAM receptor or a ligand thereto wherein a decrease in TAM receptor-mediated signaling is indicative of the presence of an inflammatory neuropathological disease or condition or a likelihood of developing same or the continued progression of the disease or condition.

Screening for upregulated levels of a TAM receptor or altered ligand expression may be by any means such as determining mRNA levels, protein levels and changes in TAM receptor-mediated signaling levels. Cell sorting and FACS may also be employed. The assay of the present disclosure may also be employed to determine minimal residual disease (MRD) in inflammatory neuropathological conditions. The use of protein or nucleic acid expression allows for a more sensitive assay.

Conveniently, blood cells are isolated and subject to an assay to determine any increase in TAM receptor levels and/or TAM receptor ligand levels. This provides a clinician with information alone or in combination with other symptoms of an inflammatory neuropathological condition including the risk or prediction of a subject developing the condition. The subject may have had an FDE or is symptomatically considered to have an inflammatory neuropathology or may be asymptomatic but is at risk of developing an FDE or other condition.

The level of TAM receptor or its ligand provides an indication of level of stress in the nervous system. It does not equate to level of signaling.

Any cell type or a range or mixture of cell types may be assayed. Hence, blood cells (such as CD3+ lymphocytes) may be collected en masse or separated and/or sorted and then assayed for TAM receptor or TAM receptor ligand mRNA or protein or TAM receptor-mediated signaling.

The present disclosure further teaches the use of a TAM receptor or TAM receptor ligand mRNA or protein in the manufacture of an assay for an inflammatory neuropathy. The inflammatory neuropathy includes an inflammatory idiopathic demyelination disease such as MS or other disorders involving oligodendrocytes. The assay components may also be packaged in kit form with compartments adapted to contain various reagents, primers and/or antibodies to quantitate or semi-quantitate the level of a TAM receptor or ligand. The kit may also contain instructions for use. The kit or assay may be used at a point of care or as part of a diagnostic protocol.

The assay may also be adapted for high through put screening for agents which agonize TAM receptor-mediated signaling. The assay may be adapted in any number of ways including genetically engineering cells to comprise a TAM receptor fused to a reporter molecule which provides an identifiable signal upon interaction with a TAM receptor ligand or mimetic or agonist. The high through put screening system may also be semi-automated to increase the ability to screen large numbers of compounds and/or to detect rare compounds.

As indicated below, the subject may be a human or test animal or may be an embryo or fetus.

The present disclosure further teaches agonists of a TAM receptor and modulators of a TAM receptor ligand or agonist of TAM receptor signaling for use in the treatment or prophylaxis of inflammatory neuropathological diseases and conditions.

The present disclosure enables, therefore, a method for the treatment or prophylaxis of an inflammatory neuropathological disease or condition in a subject, the method comprising administering to the subject an effective amount of a TAM receptor agonist or a TAM receptor ligand modulator for a time and under conditions sufficient to ameliorate the inflammatory neuropathological disease or condition. A ligand modulator may be an agonist or antagonist of ligand gene expression or ligand activity. By "ligand activity" includes the ability for the ligand to interact with the TAM receptor. In an embodiment, the ligand modulator is an agonist. In another embodiment, it is an antagonist.

The terms "compound", "active agent", "chemical agent", "pharmacologically active agent", "medicament", "active" and "drug" are used interchangeably herein to refer to such agonists which induce a desired pharmacological and/or physiological effect. The desired effect includes promoting TAM receptor-mediated signaling or modulating ligand levels or activity. This leads to inducing or promoting oligodendrocyte survival and maintenance, promotion or protection of myelination and/or protection of axons and/or neurons. The terms also encompass pharmaceutically acceptable and pharmacologically active ingredients of those active agents specifically mentioned herein including but not limited to salts, esters, amides, prodrugs, active metabolites, analogs, mimetics functional equivalents and the like. When the terms "compound", "active agent", "chemical agent" "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

Reference to a "compound", "active agent", "chemical agent" "pharmacologically active agent", "medicament", "active" and "drug" includes combinations of two or more actives such as two or more Gas6 and/or Protein S agonists or antagonists or mimetics thereof or functional equivalents thereof. A "combination" also includes multi-part such as a two-part composition where the agents are provided separately and given or dispensed separately or admixed together prior to dispensation.

The TAM receptor signaling agonists, in another embodiment, promote myelination and oligodendrocyte survival.

Reference to promoting oligodendrocyte survival includes reducing oligodendrocyte cytotoxicity or cell cycle arrest as well as promoting oligodendrocyte maintenance; promoting or protecting myelination includes inhibiting, preventing or otherwise reducing demyelination; protection of axons and neurons includes promoting axonal and neuronal repair, function and maintenance and modulating the activity of the immune system to reduce its capacity to induce damage or to otherwise promote repair. The term "cell cycle arrest" includes cytostasis or other arrest of cell growth (whether cytotoxic or not) and cell senescence.

One form of agonist is a mimetic of a TAM receptor or its ligand.

Mimetics of a TAM receptor or its ligands are proposed to have neuroprotective ability. The term is intended to refer to a substance which has some chemical similarity to the molecule it mimics and which acts as an agonist. A peptide mimetic, for example, may be a peptide-containing molecule that mimics elements of protein secondary structure (Johnson et al., Peptide Turn Mimetics in Biotechnology and Pharmacy, Pezzuto et al. (Eds), Chapman and Hall, New York, 1993). The underlying rationale behind the use of peptide mimetics is that the peptide backbone of Protein S exists chiefly to orient amino acid side chains in such a way as to facilitate molecular interactions such as with a receptor or ligand. A peptide mimetic, therefore, is designed to permit molecular interactions similar to the natural molecule.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are generally unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. Alanine scans of peptides, for example, are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of a receptor and ligand are modeled. This can be especially useful where the receptor and/or ligand change conformation on binding, allowing the model to take account of this in the design of the mimetic. Modeling can be used to generate agents which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Another form of agonist is an antibody specific for a monomeric form of a TAM receptor such as to a single chain of Axl, Mer or Tyro3 or to homomultimeric or heteromultimeric forms thereof. In an embodiment, the antibody is a monoclonal antibody or an antigen-binding fragment, chimera or deimmunized form thereof. It is proposed that antibodies to monomeric or multimeric forms of the TAM receptor promote multimerization and, hence, TAM receptor-mediated signaling. An antibody is particularly useful in promoting ligand-independent TAM receptor signaling. Reference to "an antibody" includes combinations of antibodies such as multivalent chimeric antibodies with specificity to two different targets such as two different TAM receptor monomers or heteromultimers or homomultimers.

The present disclosure further teaches the application of biochemical techniques to render an antibody derived from one animal or avian creature substantially non-immunogenic in another animal or avian creature of the same or different species. The biochemical process is referred to herein as "deimmunization". Specifically, in relation to using a non-human antibody in a human, the deimmunization may be referred to as "humanization". Reference herein to "deimmunization" or its specific form "humanization" includes processes such as complementary determinant region (CDR) grafting, "reshaping" with respect to a framework region of an immunointeractive molecule and variable (v) region mutation, all aimed at reducing the immunogenicity of an immunointeractive molecule (e.g. antibody) in a particular host (e.g. a human subject). In the present case, the preferred immunointeractive molecule is an antibody such as a polyclonal or monoclonal antibody specific for a TAM receptor monomer such as an Axl, Mer or Tyro3 monomer. In an embodiment, the immunointeractive molecule is a monoclonal antibody or a chimeric derivative of the antibody, derived from one animal or avian creature and which exhibits reduced immunogenicity in another animal or avian creature from the same or different species such as but not limited to humans. In an embodiment, the antibody has specificity to two different TAM receptor monomers to facilitate generation of heterodimers.

Reference to "substantially non-immunogenic" includes reduced immunogenicity compared to a parent antibody, i.e. an antibody before exposure to deimmunization processes. The term "immunogenicity" includes an ability to provoke, induce or otherwise facilitate a humoral and/or T-cell mediated response in a host animal. Particularly convenient immunogenic criteria include the ability for amino acid sequences derived from a variable (v) region of an antibody to interact with MHC class II molecules thereby stimulating or facilitating a T-cell mediating response including a T-cell-assisted humoral response. The deimmunization process reduces the immunogenicity of an antibody when used in a particular host.

By "antibody" is meant a protein of the immunoglobulin family that is capable of combining, interacting or otherwise associating with an antigen or two different antigens, and in particular a TAM receptor monomer such as Axl, Mer or Tyro3 or homo- or heteromultimeric forms thereof. An antibody is, therefore, an antigen-binding molecule. An "antibody" is an example of an immunointeractive molecule and includes a polyclonal or monoclonal antibody. Particular immunointeractive molecules taught herein are monoclonal antibodies. In an embodiment, the antibody is a chimera with specificity for two different monomers to facilitate generation of heterodimers.

The term "antigen" is used herein in its broadest sense to refer to a substance that is capable of reacting in and/or inducing an immune response. Reference to an "antigen" includes a peptide chain associated with Axl, Mer or Tyro3. Generally, the peptide chain in a monomer but antibodies directed to dimers or multimers of Axl, Mer and Tyro3 are also contemplated herein.

By "antigen-binding molecule" is meant any molecule that has binding affinity for a target TAM receptor. It will be understood that this term extends to immunoglobulins (e.g. polyclonal or monoclonal antibodies), immunoglobulin fragments and non-immunoglobulin derived protein frameworks that exhibit antigen-binding activity. The terms "antibody" and "antigen-binding molecules" include deimmunized forms of these molecules.

By "antigenic determinant" or "epitope" is meant that part of a TAM receptor against which a particular immune response is directed and includes a hapten. An antibody may target two different epitopes on two heteromonomers. Typically, in an animal, antigens present several or even many antigenic determinants simultaneously. A "hapten" is a substance that can combine specificity with an antibody but cannot or only poorly induces an immune response unless bound to a carrier. A hapten typically comprises a single antigenic determinant or epitope present on a portion of Axl, Mer or Tyro3 monomer.

Particular antibodies taught herein are deimmunized forms of murine monoclonal antibodies for use in humans. However, the subject disclosure contemplates antibodies from any source and deimmunized for use in any host. Examples of animal and avian sources and hosts include humans, primates, livestock animals (e.g. sheep, cows, horses, pigs, donkeys), laboratory test animals (e.g. mice, rabbits, guinea pigs, hamsters), companion animals (e.g. dogs, cats), poultry bird (e.g. chickens, ducks, geese, turkeys) and game birds (e.g. pheasants).

Desired fused cell hybrids are selected and cloned into individual antibody-producing cell lines, each cell line may be propagated in either of two standard ways. A suspension of the hybridoma cells can be injected into a histocompatible animal. The injected animal then develops tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the TAM receptor of interest by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target TAM receptor but which does not recognize non-target epitopes are identified and then directly cultured in vitro or injected into a histocompatible animal to form tumors and to produce, collect and purify the required antibodies.

Thus, the present disclosure provides in a monoclonal antibody which specifically interacts with a peptide chain from Axl, Mer or Tyro3 or a fragment thereof or with two peptide chains, one each from Axl, Mer and/or Tyro3.

The monoclonal antibody is then generally subjected to deimmunization means. Such a process may take any of a number of forms including the preparation of chimeric antibodies which have the same or similar specificity as the monoclonal antibodies prepared according to the present disclosure. Chimeric antibodies are antibodies whose light and heavy chain genes have been constructed, typically by genetic engineering, from immunoglobulin variable and constant region genes belonging to different species. Thus, in accordance with the present disclosure, once a hybridoma producing the desired monoclonal antibody is obtained, techniques are used to produce interspecific monoclonal antibodies wherein the binding region of one species is combined with a non-binding region of the antibody of another species (Liu et al., *Proc. Natl. Acad. Sci. USA* 84:3439-3443, 1987). For example, the CDRs from a non-human (e.g. murine) monoclonal antibody can be grafted onto a human antibody, thereby "humanizing" the murine antibody (European Patent Publication No. 0 239 400, Jones et al., *Nature* 321:522-525, 1986, Verhoeyen et al., *Science* 239:1534-1536, 1988 and Richmann et al., *Nature* 332:323-327, 1988). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e. at least about 85-90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

It will be understood that the deimmunized antibodies may have additional conservative amino acid substitutions which have substantially no effect on antigen binding or other immunoglobulin functions.

Exemplary methods which may be employed to produce deimmunized antibodies according to the present disclosure are described, for example, in Richmann et al., supra, 1988, Chou et al., (U.S. Pat. No. 6,056,957), Queen et al., (U.S. Pat. No. 6,180,377), Morgan et al., (U.S. Pat. No. 6,180,377) and Chothia et al., *J. Mol. Biol.* 196:901, 1987.

The antibodies may also be made to monomeric, homodimeric or heterodimeric forms of the TAM receptor monomers.

The present disclosure contemplates other molecules which can bind to a TAM receptor. The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, for example, enhance or interfere with the function of a polypeptide in vivo (see, e.g. Hodgson, *Bio Technology* 9:19-21, 1991). In one approach, one first determines the three-dimensional structure of a protein of interest by x-ray crystallography, by computer modeling or most typically, by a combination of approaches. Useful information regarding the structure of a polypeptide may also be gained by modeling based on the structure of homologous Protein S.

The terms "effective amount" and "therapeutically effective amount" of an agent as used herein mean a sufficient amount of an agent (i.e. a TAM receptor agonist) to provide the desired therapeutic or physiological effect or outcome as indicated above. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of the condition being treated, elimination of symptoms and/or underlying cause, prevention of the occurrence of symptoms of the condition and/or their underlying cause and improvement or remediation or amelioration of damage following a neurodegenerative condition. In general terms, treatment may involve actively reversing a disease or ameliorating symptoms of for example, oligodendrocyte cell death, senescence or arrest of cell growth, demyelination and/or axonal or neuronal degeneration. Amelioration of downstream physiological, psychological or mental conditions is also a useful indicator of treatment. The treatment may result in an immediate effect such as enhancing TAM receptor signaling. The treatment may also be of subjects who are asymptomatic but are at risk of developing a disease.

"Treating" a subject, therefore, may involve prevention of a condition or other adverse physiological or psychological event in a susceptible individual as well as treatment of a clinically symptomatic individual by ameliorating the symptoms of the condition or treating a clinically asymptomatic subject to reduce the risk of development of the condition.

A "subject" as used herein refers to an animal, preferably a mammal and more preferably human who can benefit from the pharmaceutical agents and formulations and methods of the present disclosure. There is no limitation on the type of animal that could benefit from the presently described pharmaceutical formulations and methods. A subject regardless of whether a human or non-human animal may be referred to as an individual, patient, animal, host or recipient. The compounds and methods taught by the present disclosure have particular applications in human medicine.

As indicated above, the preferred animals are humans but other primates such as orangutangs, gorillas and marmosets, macaques, livestock animals, laboratory test animals, companion animals or captive wild animals, as well as avian species may be useful animal models.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as avian species, zebrafish, and amphibians including *Xenopus* spp.

Whilst humans are the most important subject, non-human animals are useful animal models. In one embodiment, EAE may be induced in a non-human animal as a model to test potential neuroprotective agents.

The term "oligodendrocyte" or its plural form "oligodendrocytes" means those neural cells which provide support for axons and which produce the myelin sheath. Oligodendrocytes form segments of myelin sheaths of numerous neurons. Oligodendrocytes are a class of glial cells. The effects of the subject agents may manifest on the oligodendrocytes themselves as well as on related cells (e.g. other glial cells), precursor cells or progeny or more mature cells.

In accordance with the present disclosure, it is proposed to employ neuroprotective agents to reduce oligodendrocyte cytotoxicity or cell cycle arrest or to promote oligodendrocyte maintenance due to degenerative inflammatory processes such as immunodegenerative processes or conditions which induce cell cycle arrest.

In addition, the neuroprotective agent may reduce demyelination or promote or maintain myelination processes and/or prevent axonal or neuronal degeneration or promote axonal or neuronal repair.

Another neuroprotective agent is proposed to be an agent which up-regulates the activity of a TAM receptor. Such an agent is referred to herein as a TAM receptor agonist. Reference to a "TAM receptor" includes monomeric, homo-dimeric and hetero-dimeric forms of a TAM receptor.

Hence, the present disclosure teaches a method for the treatment or prophylaxis of a neurodegenerative disease or condition in a subject, the method comprising administering to the subject an effective amount of a TAM receptor agonist for a time and under conditions sufficient to promote survival of oligodendrocytes, inhibit demyelination and/or promote axonal and neuronal repair and function.

In another aspect, the present disclosure enables a method for the treatment of a neurodegenerative disease in a subject or at least delaying onset of symptoms thereof, the method comprising administering to the subject an effective amount of a TAM receptor agonist for a time and under conditions sufficient to promote survival of oligodendrocytes, inhibit demyelination or promote axonal and neuronal repair and function.

The present disclosure is further instructional for the treatment or prophylaxis of a neurodegenerative disease or condition resulting from one or more of oligodendrocyte cytotoxicity or cell cycle arrest, demyelination and/or disruption to axons or neurons in a subject, the method comprising administering to the subject an effective amount of a neuroprotective agent comprising a TAM receptor agonist for a time or under conditions sufficient to promote oligodendrocyte survival and/or maintenance.

As indicated above, the amount or time sufficient to treat the neurodegenerative disease or condition may be the amount or time required to ameliorate one or more symptoms of the neurodegenerative disorder. A symptom includes a psychological or mental symptom. A TAM receptor agonist includes an agonist of a TAM receptor ligand.

Neurodegenerative diseases and conditions contemplated herein include MS, acute disseminated encephalomyelitis, optic neuropathy (including neuromyelitis optic with transient autonomic disturbances) Devic's neuromyelitis optica, tropical spastic paraparesis, non-compressive myelopathies, concentric sclerosis, diffuse sclerosis acute hemorrhagic leukoencephalopathy, metabolic leukodystrophy, leukoaraiosis, acute disseminated encephalomyelitis, progressive multifocal leukoencephalopathy, multisystem atrophy and repairing the demyelination associated with disease or trauma.

MS is a particular embodiment enabled by the present disclosure.

Hence, the present disclosure enables a method for treating MS in a subject, said method comprising administering to the subject an effective amount of a TAM receptor agonist for a time and under conditions sufficient to ameliorate the symptoms of MS and/or to promote survival and/or maintenance of oligodendrocytes, inhibit demyelination and/or promote axonal or neuronal repair or function. A TAM receptor modulator (an agonist or antagonist) may alternatively be administered.

Reference to "MS in a subject" includes treating a subject with MS, potentially with MS, at risk of developing MS or who has symptoms of MS. The subject may also be asymptomatic but at risk of developing MS.

Another aspect taught by the present disclosure contemplates a method for the treatment of a MS in a subject, the method comprising administering to the subject an effective amount of a neuroprotective formulation comprising a TAM receptor agonist for a time and under conditions sufficient to promote survival of oligodendrocytes, inhibit demyelination or promote axonal and neuronal repair and function.

The TAM receptor agonist may also be provided with a neuroprotective agent such as leukemia inhibitory factor (LIF) or ciliary neurotrophic factor (CNTF).

Whilst chemical or proteinaceous agents are useful in accordance with the present disclosure, the instant methods may also be practiced using a genetic approach, Accordingly, the present disclosure teaches a method for the treatment or prophylaxis of a neurodegenerative disease or condition in a subject, the method comprising administering to the subject an effective amount of a genetic agent which increases levels of TAM receptor signaling.

The genetic agents include, for example, viral constructs which introduce cDNA or mRNA which encode a TAM receptor ligand or agonist thereof; naked cDNA or mRNA encoding a TAM receptor ligand or agonist thereof; and a RNAi or antisense construct which down-regulated inhibitors of genes encoding a TAM receptor ligand or agonist thereof.

As indicated above, the subject is generally a human and an example of a neurodegenerative disease or condition is MS.

Hence, the present disclosure teaches a pharmaceutical composition and formulation which include one or more of the agents disclosed herein. The pharmaceutical compositions enabled by the subject disclosure may be administered in a number of ways depending upon whether local or systemic treatment is desired and upon the area to be treated.

Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration; or oral administration; or via a spinal tap. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Clearly, the formulation needs to enable the agent to cross the blood brain barrier. Hence, the agent itself may need to be modified. Alternatively, the formulation may enable retrograde transport.

The pharmaceutical formulations enabled herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions taught by the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions described herein include, but are not limited to, solutions, emulsions, foams and liposome-containing formulations. The pharmaceutical compositions and formulations taught by the present disclosure may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is incorporated herein in its entirety.

Formulations described by the present disclosure include liposomal formulations. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

In one embodiment, the present disclosure employs various penetration enhancers to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on the $EC_{50}$ found to be effective in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, weekly, monthly or yearly.

The present disclosure teaches a neuroprotective formulation comprising a TAM receptor agonist or a TAM receptor ligand modulator and one or more pharmaceutically acceptable carriers and/or diluents.

In another embodiment, the disclosure enables is directed to a neuroprotective formulation comprising a TAM receptor agonist and one or both of LIF and/or CNTF and one or more pharmaceutically acceptable carriers and/or diluents.

Aspects taught herein are now described by the following non-limiting Examples.

EXAMPLE 1

Role of TAM Receptor Signaling in Demyelination

The role of TAM receptor signaling was studied in demyelination in oligodendrocyte survival and microglial activation in vitro. Additionally, the regulation of Gas6 and TAM receptors was studied during cuprizone-mediated demyelination in mice (cuprizone-mediated demyelination is described in Binder et al., 2008 supra). Finally, the influence of the loss of Gas6 upon the course of demyelination using Gas6 knockout mice was examined. In cuprizone-induced demyelination, the expression of Axl, Mer and Gas6 mRNA was increased in the corpus callosum in a temporal profile correlating with the increased infiltration and proliferation of microglial/macrophages in this model. On the other hand, expression of Tyro3 decreased, correlating with the damage and loss of oligodendrocytes. It was found that recombinant human Gas6 both promoted in vitro survival of oligodendrocytes, and reduced markers of activation in purified cultures of microglial. In Gas6 knockout mice subjected to cuprizone, demyelination was greater than in control mice, notably in the more rostral regions of the corpus callosum as assessed by luxol fast blue staining and ultrastructural analysis. Loss of myelin coincided with an increased loss of oligodendrocytes in Gas6 knockout mice. Additionally, microglial marker expression (IBA1) was increased in Gas6 knockout mice subjected to cuprizone demyelination. Together, these results show that TAM receptor activation and regulation affect demyelination by controlling both oligodendrocyte survival and microglial activation.

EXAMPLE 2

Expression Profile in MS Lesions

Quantitative PCR was used to examine the expression of transcripts encoding the genes for Axl, Mer and Tyro3 and the ligands Gas6 and Protein S. This was achieved by using RNA derived from human MS lesions (18 lesions), as well as normal appearing white matter from both MS patients (30 samples) and normal controls (15 samples). Compared to normal appearing white matter from non-MS control patients, a strong trend for an increase in expression of Mer (p=0.08), a weaker trend for an increase in expression of Axl (p=0.25), and no significant change in the expression of Tyro3, Gas6 or Protein S.

EXAMPLE 3

Expression of TAM Receptors and Ligands in T-Cells in MS

Blood was collected from 11 Patients (9 female and 2 male) presenting with their first demyelinating event. Blood was also collected from age and sex matched healthy controls. Using magnetic columns, CD3+ T-cells were collected from the blood, and from this population of cells, RNA was extracted and subsequently used in microarray analysis.

The microarray analysis showed that Axl, Mer, Gas6 and Protein S were all significantly upregulated in the MS patients compared to the healthy controls.

Using quantitative PCR on a subset of the samples used for microarray, Gas6 was shown to be significantly upregulated, with the other genes following the same trend observed in the microarray.

EXAMPLE 4

Demyelination in Gas6 Knockout Mice

Figure 3:
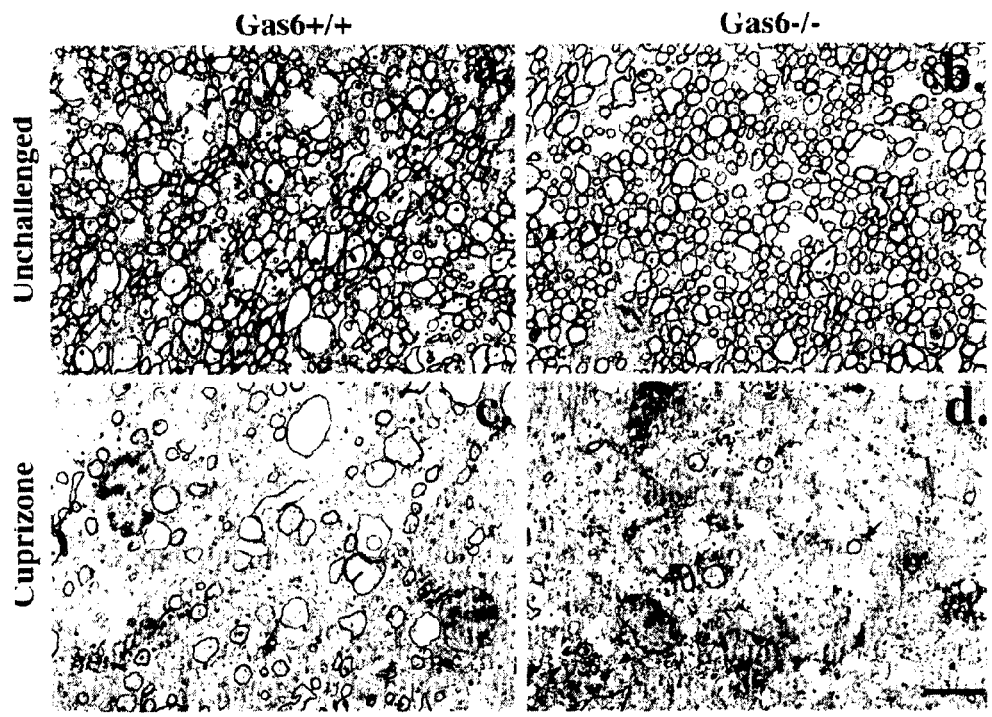
FIG. 3 is a photographic representation of cuprizone versus unchallenged Gas6 knock out (Gas6$^{-/-}$) mice showing effects on demyelination.
Figure 4:
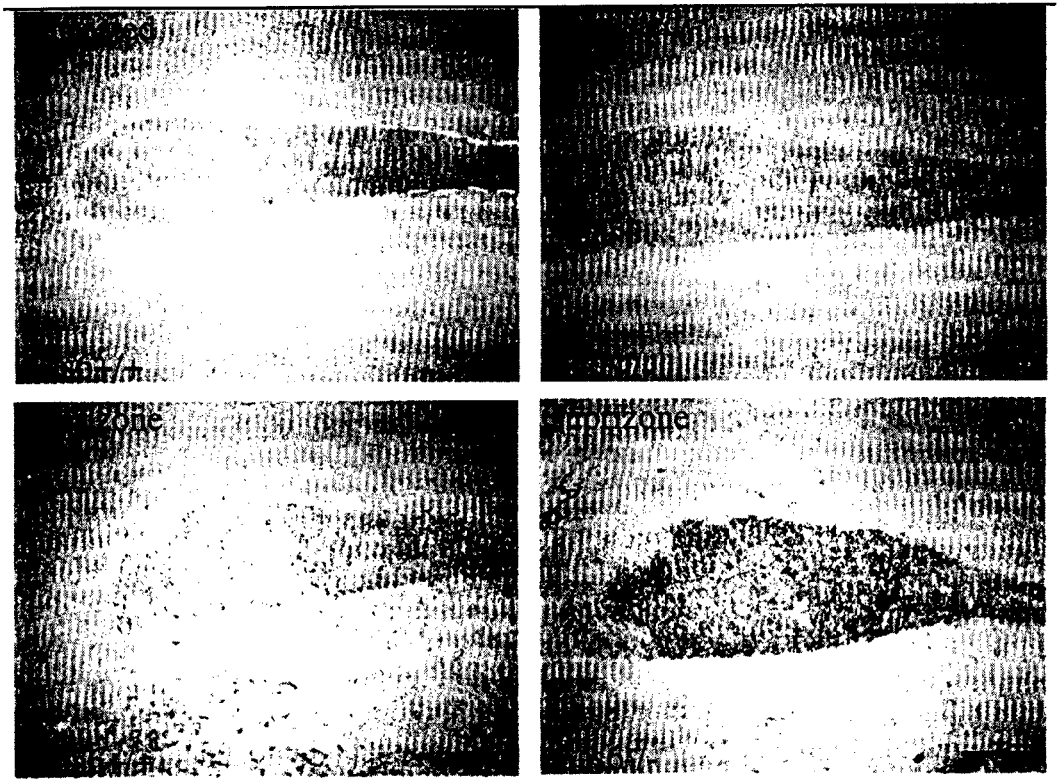
FIG. 4 is a photographic representation of cuprizone versus unchallenged Gas6 knock out (Gas6$^{-/-}$) mice showing effects on microglial activation and infiltration.

FIG. 3 shows the demyelination is greater in the absence of Gas6 and there are fewer Gst-pi positive oligodendrocytes. FIG. 4 shows that microglial activation and infiltration is greater in the absence of Gas6 during cuprizone-induced demyelination.

EXAMPLE 5

Remyelination in Gas6 Knock Out Mice

Luxol fast blue (LFB) mean density was lower after 4 weeks recovery in the absence of Gas6.
G ratios were unaffected during this period.
In addition, fewer myelinated axons were observed after the 4 week recovery in the absence of Gas6.

EXAMPLE 6

In Vitro Myelination with Gas6

Figure 5A:
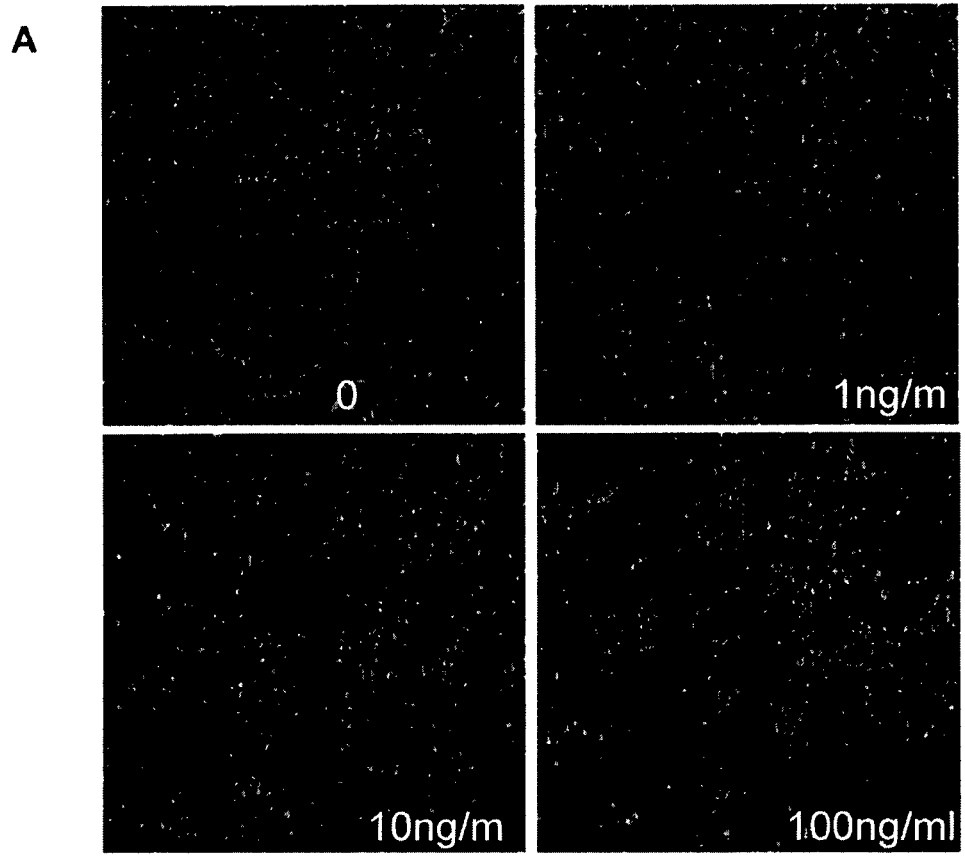

FIGS. 5A through C show that exogenous Gas6 increased myelination in vitro.

EXAMPLE 7

TAM Receptor Signaling in EAE-Induced Demyelination

Figure 6A:
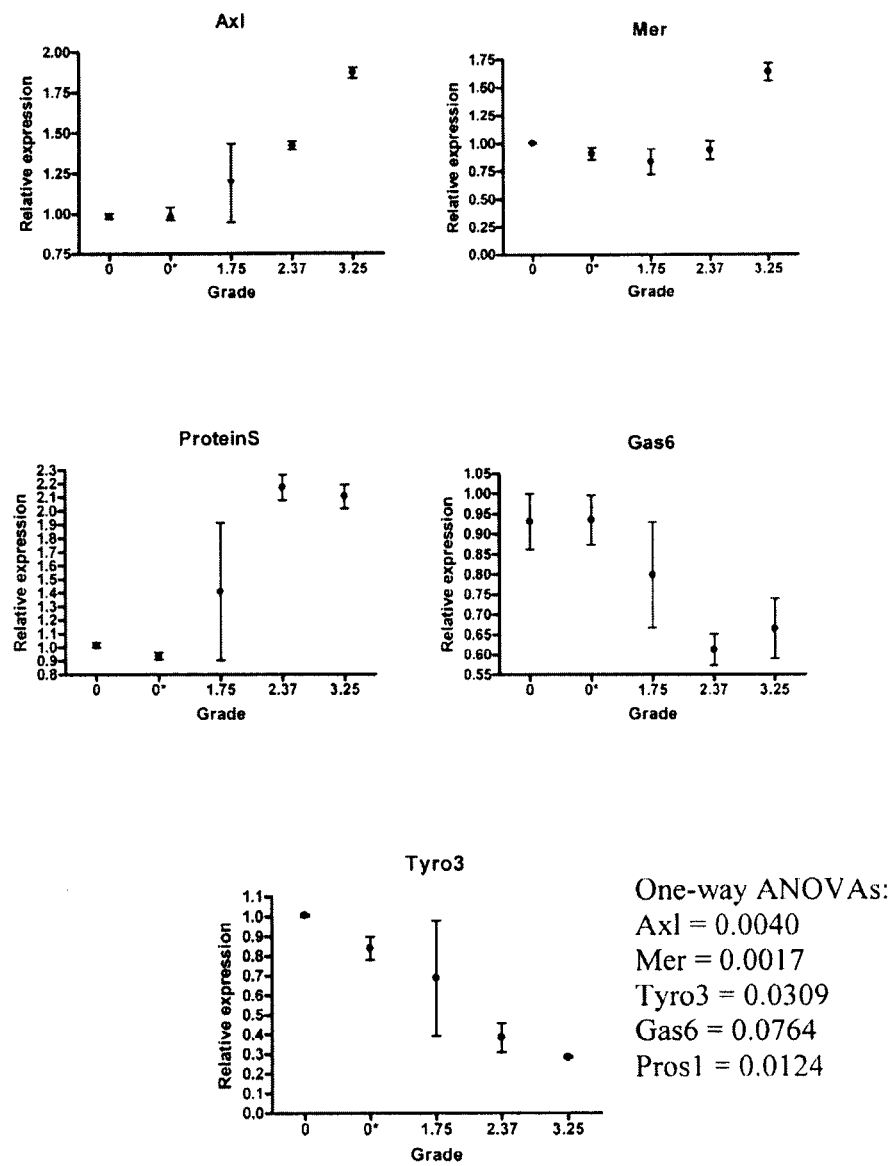
FIGS. 6A through C are graphical representations showing that TAM receptors and ligands are regulated during EAE and that expression or levels are correlated with measures of cellular change.
Figure 6B:
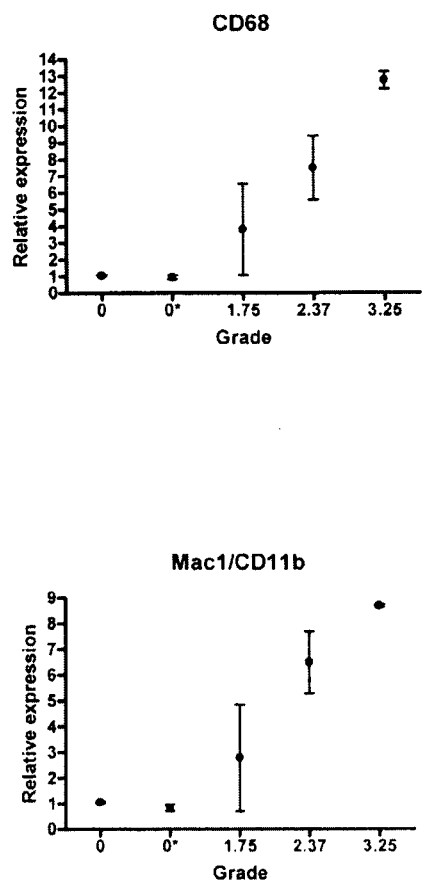
Figure 6C:
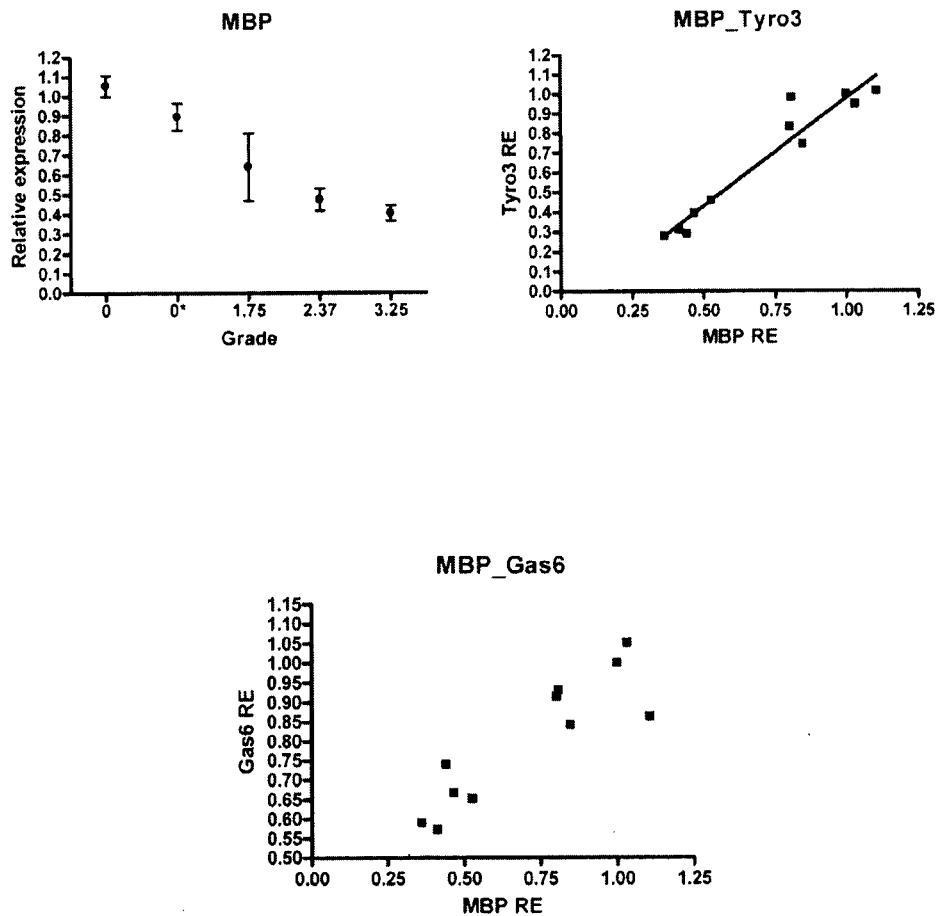

FIGS. 6A through C show that TAM receptors and ligands are regulated during EAE and expression levels were correlated with measures of cellular change.

EXAMPLE 8

Oligodendrocyte Loss and Inflammation is Increased, and Recovery Inhibited, During Cuprizone-Induced Demyelination in Mice Lacking Gas6

In order to examine the influence of the loss of Gas6 on the course of demyelination, wild-type and Gas6 knockout mice were challenged with cuprizone (0.2% w/v) for three weeks. Myelination was measured histologically (luxol fast blue; LFB) and at the ultrastructural level. Immunohistochemistry was used to assess oligodendrocyte number (Gst-pi) and microglial activity (IBA1). These studies were extended to examine the influence of the absence of Gas6 on the recovery phase after the withdrawal of cuprizone. For recovery studies, mice were subjected to cuprizone challenge for 5 weeks. One group was analysed at this time-point to provide nadir levels of myelination and oligodendrocyte numbers. The remaining mice were analysed at either two, four or ten weeks post-cuprizone withdrawal. Myelination and cellular responses were assessed as for demyelination studies. The influence of Gas6 on survival and activation of primary microglia was assessed using quantitative PCR. The response of rat oligodendrocytes to exogenous Gas6 was assessed using in vitro myelination assays.

The expression of the Gas6 gene and the genes for its receptors, Tyro3, Axl and Mer were found to be regulated during the course of cuprizone-induced demyelination. The expression profiles of Axl, Mer and Gas6 mRNA were increased in the corpus callosum in a temporal profile correlating with the increased infiltration and proliferation of microglia/macrophages in this model. On the other hand, expression of Tyro3 decreased, correlating with the damage and loss of oligodendrocytes. In Gas6 knockout mice subjected to cuprizone induced demyelination for 3 weeks demyelination was greater than in control mice, notably in the more rostral regions of the corpus callosum (myelination reduced by 36% in 3 week cuprizone challenged Gas6 knockout vs wild type mice; p=0.027) as assessed by both luxol fast blue staining and increased in Gas6 knockout mice subjected to cuprizone demyelination (~3 fold increase; p<0.05). In vitro, it was found that recombinant human Gas6 (100 ng/ml) promoted both the survival of oligodendrocytes (39.3±3.1% vs 11.8±2.4%; p=$4.6 \times 10^{-5}$) and reduced markers of activation in purified cultures of microglia (TNFα expression reduced ~48%; p<0.05).

In the recovery studies, after 5 weeks of cuprizone challenge, demyelination was greater in Gas6 knockout mice than control mice, as assessed by both luxol fast blue staining and ultrastructure. However, by two weeks post-cuprizone withdrawal there was no significant difference between genotypes (p<0.05). However, after 4 weeks recovery in the absence of cuprizone, WT mice had remyelinated to a significantly greater extent than Gas6 KO mice (p=0.04). To understand the molecular mechanisms that drive the observed effects the effect of exogenous Gas6 in in vitro myelination assays was also examined. It was found that Gas6 significantly increased myelination in a dose-dependent manner (p=0.02), suggesting that TAM receptor signalling could be directly involved in myelination by oligodendrocytes.

The increased loss of Gst-pi (glutathione-S-transferase-pi) positive oligodendrocytes identified in the corpus callosum of Gas6 knockout mice, along with increased IBA1 positive microglia, indicate that TAM receptor regulation and activation can influence both oligodendrocyte survival and microglial activation during CNS demyelination. This conclusion is supported by the in vitro data showing exogenous Gas6 can both increase survival in primary oligodendrocytes and decrease microglial activation.

Further, it was shown that in the absence of Gas6, initial remyelination after the withdrawal of cuprizone is comparable to that observed in wild-type mice, but that continued recovery appears to be compromised. It was also shown in vitro that TAM receptor signalling could be directly involved in myelination by oligodendrocytes. The failure of Gas6 KO mice to fully remyelinate could thus result from a lack of Gas6 at a critical time during myelin production after injury. To address these issues further, levels of oligodendrocyte progenitor recruitment the microglial activation are being assessed, completing a detailed ultrastructural analysis of myelin integrity, as well as assessing later stages of remyelination, following cuprizone challenge in Gas6 KO mice.

EXAMPLE 9

Generation of TAM Receptor Antibodies

It is proposed herein to use monoclonal antibodies to a monomeric form of Axl, Mer and/or Tyro3 or to heterodimeric or homodimeric forms or derivatives thereof to promote multimerization such as dimerization and therefore signaling. Recombinant Tyro3, Axl and/or Mer chains are generated and used to generate monoclonal antibodies in mice or rabbits as herein described. The antibodies are then subjected to deimmunization or humanization for trials in human subjects.

Immunization and subsequent production of monoclonal antibodies is carried out using standard protocols as for example described by Köhler and Milstein (Kohler et al., *Nature* 256:495-499, 1975 and Kohler et al., *Eur. J. Immunol.* 6(7):511-519, 1976, Coligan et al., *Current Protocols in Immunology*, 1991-1997 or Toyama et al., *Monoclonal Antibody, Experiment Manual*, published by Kodansha Scientific, 1987). Essentially, an animal is immunized with an antigen-containing (e.g. TAM receptor containing sample) or fraction thereof by standard methods to produce antibody-producing cells, particularly antibody-producing somatic cells (e.g. B lymphocytes). These cells are then removed from the immunized animal for immortalization. The antigen may need to first be associated with a carrier.

Immortalization of antibody-producing cells is carried out using methods which are well-known in the art. For example, the immortalization may be achieved by the transformation method using Epstein-Barr virus (EBV) [Kozbor et al. *Methods in Enzymology* 121:140, 1986]. In an embodiment, antibody-producing cells are immortalized using the cell fusion method (described in [Coligan et al., supra, 1991-1997]), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In an embodiment, mice spleen cells are used. It would be possible, however, to use rat, rabbit, sheep or goat cells, or cells from other animal species instead.

Specialized myeloma cell lines have been developed from lymphocytic tumors for use in hybridoma-producing fusion procedures (Kohler et al., supra, 1976, Kozbor et al., supra, 1986 and Volk et al., *J. Virol.* 42(1):220-227, 1982). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumour cells to produce their own antibodies. To eliminate the production of tumour cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4-1 (NS-1), Sp2/0-Ag14 and S194/5.XXO.Bu.1 (Trowbridge, *J. Exp. Med.* 148(1):220-227, 1982). The P3X63-Ag8 and NS-1 cell lines have been described by Köhler and Milstein (Kohler et al., supra, 1976). Shulman et al., *Nature* 276:269-270, 1978, developed the Sp2/0-Ag14 myeloma line.

Fusion methods have been described (Kohler et al., supra, 1975, Kohler et al., supra, 1976, Gefter et al., *Somatic Cell Genet.* 3:231-236, 1977 and Volk et al., supra, 1982). The fusion-promoting agents used by those investigators were Sendai virus and polyethylene glycol (PEG).

Those skilled in the art will appreciate that aspects described herein are susceptible to variations and modifications other than those specifically described. It is to be understood that these aspects include all such variations and modifications. The instant disclosure enables all of the steps, features, compositions and compounds referred to or indicated in this specification, individually or collectively, and any and all combinations of any two or more of these steps or features.

BIBLIOGRAPHY

Barkinof et al., *Brain* 120:2059-2069, 1997
Barnett and Prineas, *Ann. Neurol* 55:459-468, 2004
Binder et al., *The Journal of Neuroscience* 28(2):5195-5206, 2008
Brex et al., *N. Engl. J. Med* 346(3):158-164, 2002
Coligan et al., *Current Protocols in Immunology*, 1991-1997
Gefter et al, *Somatic Cell Genet.* 3:231-236, 1977
Hodgson, *Bio Technology* 9:19-21, 1991
Johnson et al., *Peptide Turn Mimetics in Biotechnology and Pharmacy*, Pezzuto et al (Eds), Chapman and Hall, New York, 1993
Jones et al., *Nature* 321:522-525, 1986
Kohler et al., *Nature* 256:495-499, 1975
Kohler et al., *Eur. J. Immunol.* 6(7):511-519, 1976
Kozbor et al., *Methods in Enzymology* 121:140, 1986
Lai and Lemke, *Neuron* 6:691-704, 1991
Lemke and Rothlin, *Nature Reviews (Immunology)* 8:327-336, 2008
Liu et al, *Proc. Natl. Acad. Sci. USA* 84:3439-3443, 1987
O'Riorden et al., *Brain* 121:495-503, 1998
Richmann et al., *Nature* 332:323-327, 1988
Shulman et al., *Nature* 276:269-270, 1978
Toyama et al., *Monoclonal Antibody, Experiment Manual*, published by Kodansha Scientific, 1987
Trowbridge, *J. Exp. Med.* 148(0:220-227, 1982
Verhoeyen et al., *Science* 239:1534-1536, 1988
Volk et al., *J. Virol.* 42(0:220-227, 1982

The invention claimed is:

1. A method for increasing myelination by oligodendorcytes and decreasing activation of microglia microglia, said method comprising administering an effective amount of Gas6 to the oligodendrocytes and to the microglia for a time and under conditions sufficient to increase said myelination and decrease said activation.

2. The method of claim 1, wherein the oligodendrocytes and microglia are human oligodendrocytes and microglia.

* * * * *